United States Patent [19]  [11] 3,933,466
Fischer  [45] Jan. 20, 1976

[54] URACIL AND CARBAMATE HERBICIDE MIXTURES

[75] Inventor: Adolf Fischer, Mutterstadt, Germany

[73] Assignee: BASF Aktiengesellschaft, Ludwigshafen (Rhine), Germany

[22] Filed: July 30, 1974

[21] Appl. No.: 493,114

[60] Related U.S. Application Data
Division of Ser. No. 348,085, Apr. 4, 1973.

[30] Foreign Application Priority Data
Apr. 13, 1972 Germany............................ 2217698

[52] U.S. Cl................................. 71/92; 71/111
[51] Int. Cl.²............................................ A01N 9/22
[58] Field of Search............................ 71/92, 111

[56] References Cited
UNITED STATES PATENTS

| | | | |
|---|---|---|---|
| 3,235,363 | 2/1966 | Luckenbaugh et al. | 71/92 |
| 3,436,207 | 4/1969 | Soboczenski | 71/92 |
| 3,551,477 | 12/1970 | Koenig et al. | 71/111 |
| 3,692,820 | 9/1972 | Boroschewski et al. | 71/111 |
| 3,758,477 | 9/1973 | Zeidler et al. | 71/92 |

Primary Examiner—Lewis Gotts
Assistant Examiner—Catherine N. Mills
Attorney, Agent, or Firm—Johnston, Keil, Thompson & Shurtleff

[57] ABSTRACT

Herbicide compositions embodying mixtures of (a) 3-cyclohexyl-5,6-trimethylene uracil, (b) 3-methoxycarbonylaminophenyl-N-3'-(methylphenyl)-carbamate and herbicidal uses thereof.

1 Claim, No Drawings

URACIL AND CARBAMATE HERBICIDE MIXTURES

RELATED APPLICATION

This application is a division of my copending application Ser. No. 348,085, filed Apr. 4, 1973, the disclosure of which is incorporated herein by reference.

The present invention relates to a herbicide comprising a composition of a herbicidally active mixture of a uracil and a carbamate.

It is known to use methane sulfonates, pyridazones, uracils and carbamates for controlling broadleaved and grassy weeds. However, their action is poor.

I have now found that a composition of
a. a compound of the formula

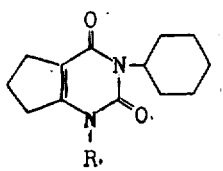

where R denotes hydrogen, and
b. a compound of the formula

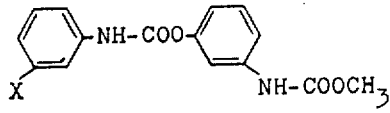

where X denotes methyl, has a good herbicidal action.

The active ingredients may be mixed in any ratio; it is however preferred to empoly a ratio of a : b of from 10 : 1 to 1 : 10. The herbicide compositions suppress growth of undesired or weed plants in crop plants by application to the loci of the plants, i.e., the host soil for the plants or to the plants themselves, of a herbicidally effective amount of the mixture of a and b.

The agent according to the invention may be used as solutions, emulsions, suspensions, oil dispersions, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons such as tetrahydronaphthalene and alkylated naphthalenes are suitable.

Aqueous formulations may be prepared from emulsion concentrates, pastes or wettabble powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent. Oils of various types may be added to ready-to-use spray liquors.

Dusts may be prepared by mixing or grinding the active ingredients with a solid carrier, e.g., kieselguhr, talc, clay or fertilizers.

Granules may be prepared by bonding the active ingredients to solid carriers.

Directly sprayable dispersions may also be prepared with oils.

The new compounds may be mixed with fertilizers, insecticides, fungicides and other herbicides.

The new herbicides may be applied either pre- or postemergence, and are particularly suited for controlling dicotyledonous seed weeds and monocotyledonous seed grasses in crops such as beet, spinach, potatoes, peas, beans and groundnuts.

EXAMPLE 1

In the greenhouse, various plants were treated at a growth height of 3 to 12 cm with the following amounts of the following active ingredients and compositions thereof as emulsions:

I 3-cyclohexyl-5,6-trimethylene uracil, 0.1, 0.25, 0.5, 0.75, 1.0 and 1.1 kg/ha;

II 3-methoxycarbonylaminophenyl-N-(3'-methylphenyl)-carbamate, 0.1, 0.25, 0.5, 0.75, 1.0 and 1.1 kg/ha;

I + II 0.25+0.25, 0.25+0.75, 0.75+0.25, 0.5+0.5, 0.1+1.0 and 1.0+0.1 kg/ha.

After 2 to 3 weeks it was ascertained that the compositions had a better herbicidal action than their individual components, combined with the same good crop plant compatibility.

The results are given below:

| Active ingredients kg/ha | I | | | | | | II | | | | | |
|---|---|---|---|---|---|---|---|---|---|---|---|---|
| | 0.1 | 0.25 | 0.5 | 0.75 | 1.0 | 1.1 | 0.1 | 0.25 | 0.5 | 0.75 | 1.0 | 1.1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 2 | 5 | 10 | 20 | 30 | 32 | 2 | 5 | 10 | 15 | 20 | 22 |
| Bromus tectorum | 3 | 10 | 20 | 25 | 35 | 37 | 2 | 3 | 8 | 12 | 15 | 16 |
| Matricaria chamomilla | 4 | 10 | 20 | 30 | 40 | 42 | 5 | 10 | 18 | 25 | 35 | 38 |
| Setaria faberii | 3 | 15 | 20 | 25 | 35 | 37 | 3 | 6 | 10 | 15 | 20 | 21 |
| Sinapis arvensis | 12 | 20 | 30 | 35 | 65 | 68 | 8 | 16 | 35 | 50 | 75 | 80 |

0 = no damage
100 = complete destruction

| Active ingredients kg/ha | I + II | | | | | |
|---|---|---|---|---|---|---|
| | 0.25+0.25 | 0.25+0.75 | 0.75+0.25 | 0.5+0.5 | 0.1+1.0 | 1.0+0.1 |
| Crop plants: | | | | | | |
| Beta vulgaris | 0 | 0 | 0 | 0 | 0 | 0 |
| Unwanted plants: | | | | | | |
| Avena fatua | 30 | 55 | 60 | 50 | 50 | 60 |
| Bromus tectorum | 40 | 60 | 63 | 61 | 55 | 65 |
| Matricaria chamomilla | 45 | 65 | 70 | 62 | 75 | 78 |
| Setaria faberii | 46 | 68 | 70 | 65 | 67 | 70 |
| Sinapis arvensis | 60 | 95 | 85 | 93 | 100 | 100 |

0 = no damage
100 = complete destruction

Similar results may be obtained with mixtures of like weight ratio wherein compound I is:
1-acetyl-3-cyclohexyl-5,6-trimethylene uracil;
1-propionyl-3-cyclohexyl-5,6-trimethylene uracil; or
α,α-dimethyl-β-acetoxypropionyl-3-cyclohexyl-5,6-trimethylene uracil; and/or compound II is
3-methoxycarbonylaminophenyl-N-phenylcarbamate;
3-methoxycarbonylaminophenyl-N-(3'-methylphenyl)-carbamate; or
3-methoxycarbonylaminophenyl-N-(3'-propylphenyl)-carbamate.

I claim:
1. A herbicide composition containing a herbicidally effective amount of a mixture of (a) 3-cyclohexyl-5,6-trimethylene uracil and (b) 3-methoxycarbonylaminophenyl-N-(3'-methylphenyl)-carbamate in a weight ratio of a to b in the range of 10:1 to 1:10.

* * * * *